(12) United States Patent
Stamp

(10) Patent No.: US 9,211,127 B2
(45) Date of Patent: Dec. 15, 2015

(54) ORTHOPAEDIC SURGICAL INSTRUMENT

(71) Applicant: Orchid MPS Holdings, LLC, Holt, MI (US)

(72) Inventor: Kevin Stamp, Sheffield (GB)

(73) Assignee: ORCHID MPS HOLDINGS, LLC, Holt, MI (US)

( * ) Notice: Subject to any disclaimer, the term of this patent is extended or adjusted under 35 U.S.C. 154(b) by 276 days.

(21) Appl. No.: 13/800,340

(22) Filed: Mar. 13, 2013

(65) Prior Publication Data

US 2013/0267957 A1    Oct. 10, 2013

Related U.S. Application Data

(63) Continuation of application No. 11/997,358, filed as application No. PCT/GB2006/003029 on Aug. 14, 2006, now Pat. No. 8,407,880.

(30) Foreign Application Priority Data

Aug. 15, 2005    (GB) .................................. 0516625.1

(51) Int. Cl.
   *A61B 17/00* (2006.01)
   *A61B 17/16* (2006.01)
(52) U.S. Cl.
   CPC ......... *A61B 17/1615* (2013.01); *A61B 17/1666* (2013.01); *A61B 2017/0023* (2013.01); *A61B 2017/00526* (2013.01); *Y10T 29/4998* (2015.01); *Y10T 29/49986* (2015.01)
(58) Field of Classification Search
   CPC combination set(s) only.
   See application file for complete search history.

(56) References Cited

U.S. PATENT DOCUMENTS

| 4,621,637 A | 11/1986 | Fishbein |
| 4,811,632 A | 3/1989 | Salyer |
| 5,100,267 A | 3/1992 | Salyer |
| 5,302,234 A | 4/1994 | Grace et al. |
| 5,709,688 A | 1/1998 | Salyer |
| 5,897,558 A | 4/1999 | Frieze et al. |
| 6,730,094 B2 | 5/2004 | Salyer et al. |
| 6,951,563 B2 | 10/2005 | Wolford |

(Continued)

FOREIGN PATENT DOCUMENTS

| EP | 0574701 A1 | 5/1993 |
| EP | 1611854 A1 | 1/2006 |

(Continued)

OTHER PUBLICATIONS

Communication of European Patent Office dated Aug. 4, 2010 in European Patent Application No. 06765280.0-2310 corresponding to International Patent Application No. PCT/GB2006/003029.
Communication of European Patent Office dated Dec. 8, 2010 in European Patent Application No. 06765280.0-2310 corresponding to International Patent Application No. PCT/GB2006/003029.
International Preliminary Report on Patentability and Written Opinion for International Patent Application No. PCT/GB2006/003029 issued Feb. 20, 2008.
International Search Report for International Patent Application No. PCT/GB2006/003029.

*Primary Examiner* — Christopher Beccia
*Assistant Examiner* — Diana S Jones
(74) *Attorney, Agent, or Firm* — Gardner, Linn, Burkhart & Flory, LLP

(57) ABSTRACT

An orthopaedic surgical instrument comprising an internal support about which a plastic substrate is disposed, and which includes exposed cutting surfaces relative to the plastic substrate. The surgical instrument may have a generally hemispherical shape and the internal support may comprise a non-planar shim. In particular embodiments the shim includes multiple interconnected limbs with multiple holes or slots disposed in the limbs and with the holes or slots including the cutting surfaces.

20 Claims, 14 Drawing Sheets

(56) References Cited

U.S. PATENT DOCUMENTS

| | | |
|---|---|---|
| 7,097,646 B2 | 8/2006 | Schantz |
| 7,118,575 B2 | 10/2006 | Wolford |
| 7,220,264 B1 * | 5/2007 | Hershberger .................. 606/81 |
| 2003/0181916 A1 | 9/2003 | Wolford |
| 2004/0225294 A1 | 11/2004 | Frederick et al. |
| 2004/0249383 A1 | 12/2004 | White et al. |
| 2005/0113837 A1 | 5/2005 | Salyer |
| 2005/0203525 A1 | 9/2005 | White et al. |
| 2006/0004371 A1 | 1/2006 | Williams, III et al. |
| 2006/0095041 A1 | 5/2006 | Fehlbaum et al. |
| 2007/0276394 A1 * | 11/2007 | Johnson et al. ................. 606/80 |
| 2009/0163921 A1 | 6/2009 | Lechot et al. |
| 2013/0245628 A1 * | 9/2013 | Sidebotham et al. .......... 606/80 |

FOREIGN PATENT DOCUMENTS

| | | |
|---|---|---|
| FR | 2847453 A1 | 11/2002 |
| FR | 2928533 A1 | 3/2008 |
| WO | 2007097749 A1 | 8/2007 |

* cited by examiner

ORTHOPAEDIC SURGICAL INSTRUMENT

CROSS REFERENCE TO RELATED APPLICATION

This application is a continuation of U.S. application Ser. No. 11/997,358, which is a national stage application under 35 U.S.C. 371 of PCT Application No. PCT/GB2006/003029 having an international filing date of Aug. 14, 2006, which designates the United States, which PCT application claimed the benefit of United Kingdom Application Serial No. 0516625.1, filed Aug. 15, 2005, the entire disclosure of each of which is hereby incorporated herein by reference This invention relates to the field of instruments used in orthopaedic surgery for example, but not limited to, acetabular reamers, femoral reamers, broaches/rasps etc. The present invention may be equally applicable to other instruments used in hip, knee, spinal, shoulder, elbow, trauma and toe surgery, for example.

BACKGROUND

Acetabular reamers are surgical tools which are used to cut hemispherical cavities in pelvis bones for the insertion of artificial hip joints. The reamer comprises a hemispherical reamer cup, made from surgical stainless steel, having a complex arrangement of cutting surfaces extending outwardly from the hemispherical cup. The reamer cup is attachable to a drive shaft or handle, which in turn can be attached to a drill or the like to provide rotational force.

Acetabular reamers must be capable of producing cavities of very precise dimensions and consequently, the cutting surfaces are generally drilled, worked and sharpened by hand in order to give the required precision. Therefore the manufacturing process for conventional acetabular reamer cups is very skilled, labour-intensive and hence so expensive that it is not economical for the reamer to be disposable. This means that the reamer cup must be intensively cleaned after each use. The cutting surfaces may periodically require re-sharpening as a result of wear in use and/or during cleaning, the re-sharpening being a labour-intensive and skilled task in itself. An example of such a conventional reamer is described in U.S. Pat. No. 4,811,632.

Not only must the reamer cup be cleaned after each use, but also the reusable handle or drive shaft. The junction between the reamer cup and the drive shaft or handle is particularly difficult to clean as it may trap bone particles, dried blood and/or other debris. The interior of the reamer cup described in U.S. Pat. No. 4,811,632 has a cylindrical surface which engages coaxially with the drive shaft, the two being removably secured together by means of a pair of pins extending through holes therein. Alternatively, the reamer cup could be mounted to the drive shaft by engaging threads or discrete fasteners or other equivalent means. All of these moving parts and components provide locations where debris could become trapped, presenting contamination risk and/or problems in fitting the parts together. Undesirable free play between the cup and drive shaft increases wear and decreases the precision of the reamer.

Therefore, it is desirable to provide a simplified and preferably disposable reamer such as that described in U.S. Pat. No. 5,100,267. In U.S. Pat. No. 5,100,267, a disposable reamer cup is provided for use with a reusable drive shaft or handle, wherein the reamer cup is provided with a polymeric plug into which the drive shaft is fitted. The polymeric plug is joined to the reamer cup by detents and intrusions thereon. The drive shaft is attached to the polymeric plug in the same manner as described in U.S. Pat. No. 4,811,632 and, although containing less metal because of the use of the polymeric plug, the reamer cup is manufactured in the same way as described in U.S. Pat. No. 4,811,632.

Consequently, the metal reamer cup is still made using a labour-intensive method, necessary in order to provide the accurately placed cutting surfaces. Furthermore, the number of moving parts and components in the junction between the reamer cup and the drive shaft is not addressed.

It is therefore desirable to provide an improved disposable acetabular reamer or other surgical instrument which seeks to alleviate the disadvantages of the above-described prior art.

SUMMARY OF THE INVENTION

According to a first aspect of the present invention there is provided a method of manufacturing an orthopaedic surgical instrument comprising the steps of forming a generally planar shim having a predetermined shape;

creating a plurality of holes or slots in the plane of the shim;

temporarily shielding said holes or slots from a plastic moulding process;

overmoulding said shim with a plastic substrate using said plastic moulding process;

creating a cutting surface at each of said holes or slots.

Preferably the step of creating the cutting surfaces occurs before said shielding and overmoulding steps. Alternatively, the cutting surfaces can be created after overmoulding, as a final step in the manufacture of the orthopaedic surgical instrument.

Preferably, said plastic moulding process is injection moulding and/or said plastic is free-flowing acetal.

In a preferred embodiment, said plastic substrate is moulded to at least part of the exterior surface of said shim. Alternatively, said shim is encapsulated by said plastic substrate i.e. having plastic moulded to both the exterior and interior surfaces of said shim. A further alternative embodiment, in which the substrate is moulded to a peripheral flange is described below.

Preferably, said holes or slots are created by pressing or punching through said shim. The cutting surfaces may also be created by pressing or punching through said shim, or alternatively the cutting surfaces may be formed using a broach. The shim is preferably metal, preferably surgical stainless steel or titanium but may also be made from suitable plastics e.g. PEEK.

In a preferred embodiment, said holes or slots and/or cutting surfaces are temporarily shielded from said plastic moulding process using a mould tool of complementary shape to said shim and said holes or slots and/or cutting surfaces.

Preferably, the method further comprises the step of bending said shim into a non-planar shape before overmoulding the plastic substrate. Separately, or in a simultaneous bending step, the method may further comprise the step of bending said shim to form a peripheral flange thereon with a raised section therebetween.

In one embodiment, the orthopaedic surgical instrument is an acetabular reamer cup and wherein said non-planar shape is a generally hemispherical shape.

In a preferred embodiment, the plastic substrate is moulded to the exterior surface of the peripheral flange, preferably so that the upper surface of the substrate is substantially flush with the raised section of the shim. In this way, the cutting surfaces (or the holes/slots where the cutting surfaces will be formed) are fully exposed and free of plastic.

Preferably, said generally planar shim is a cross-shape. However, this is non-limiting any suitable shape for the shim can be selected according to the circumstances, as can the number and location of the holes or slots and/or cutting surfaces provided thereon.

According to a second aspect of the invention, there is provided a surgical instrument manufactured using the method of any of the preceding paragraphs. Preferably, the surgical instrument is an acetabular reamer cup.

BRIEF DESCRIPTION OF THE DRAWINGS

Preferred embodiments of the present invention will now be more particularly described, by way of example only, with reference to the accompanying drawings in which.

DETAILED DESCRIPTION

Throughout the description and claims of this specification, the words "comprise" and "contain" and variations of the words, for example "comprising" and "comprises", means "including but not limited to", and is not intended to (and does not) exclude other components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, or groups thereof described in conjunction with a particular aspect, embodiment or example of the invention are to be understood to be applicable to any other aspect, embodiment or example described herein unless incompatible therewith.

Throughout this description, the term "shim" is used to describe any relatively thin, generally flat or planar item, preferably made from metal, which is used as a template or blank to form the basis of the instrument manufactured according to the method described herein. This description is provided solely to aid the reader and should not be construed to have a scope less than that understood by a person skilled in the art or as limiting the scope of the appended claims.

Figure 1:
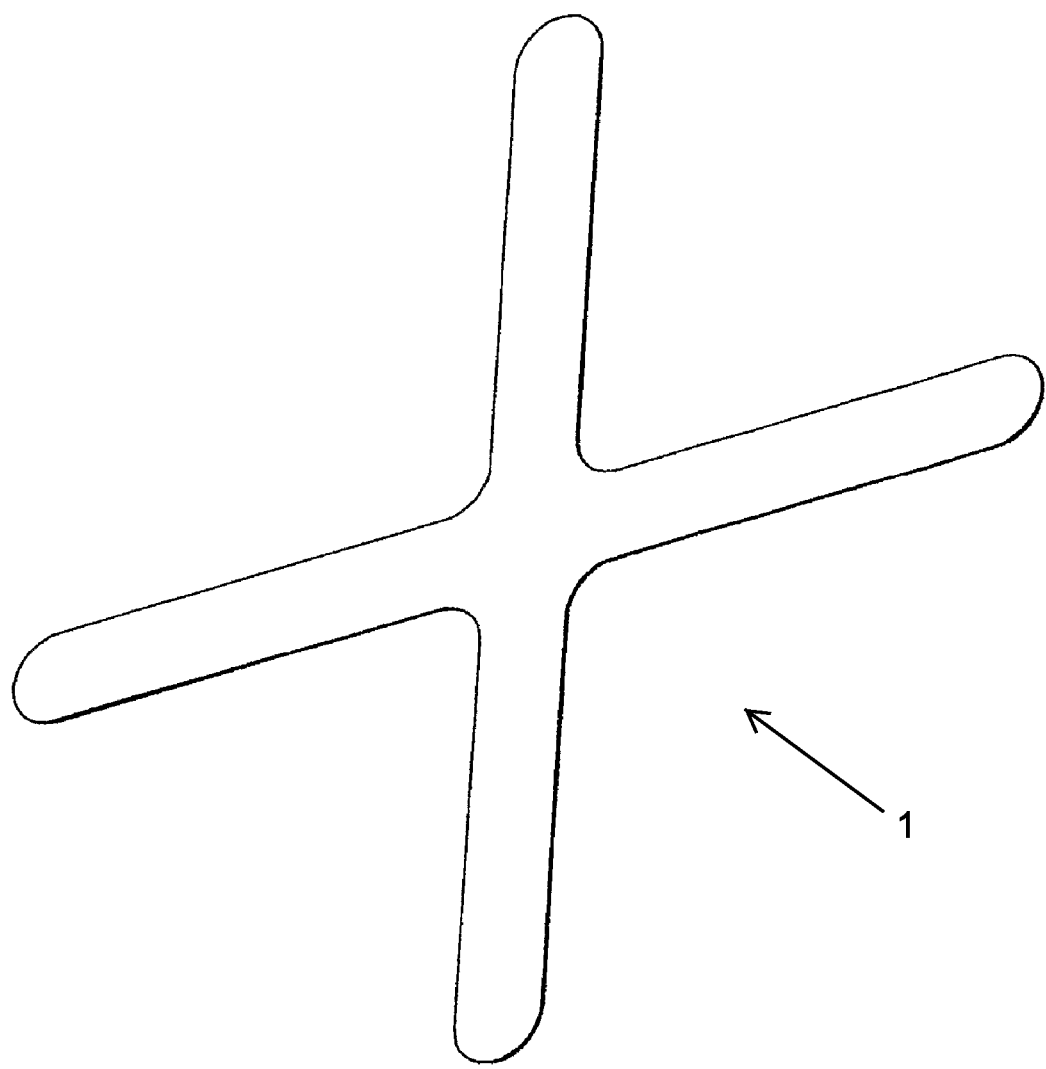
FIG. 1 is a perspective view of a metal shim for use in the method of the present invention.

Referring to FIG. 1, a generally planar shim 1 is pressed from a sheet of metal. The shim could be any desired shape but, in the illustrated embodiment, is generally cross-shaped. A cross-shaped shim need not have equal angles between all four of its limbs. Suitable metals include surgical stainless steel or titanium, for example, and the metal sheet from which the shim 1 is pressed is typically of 0.2-0.5 mm thickness. Alternatively, instead of metal, the shim could be formed from a suitable plastic such as PEEK (polyetheretherketone).

Figure 2:
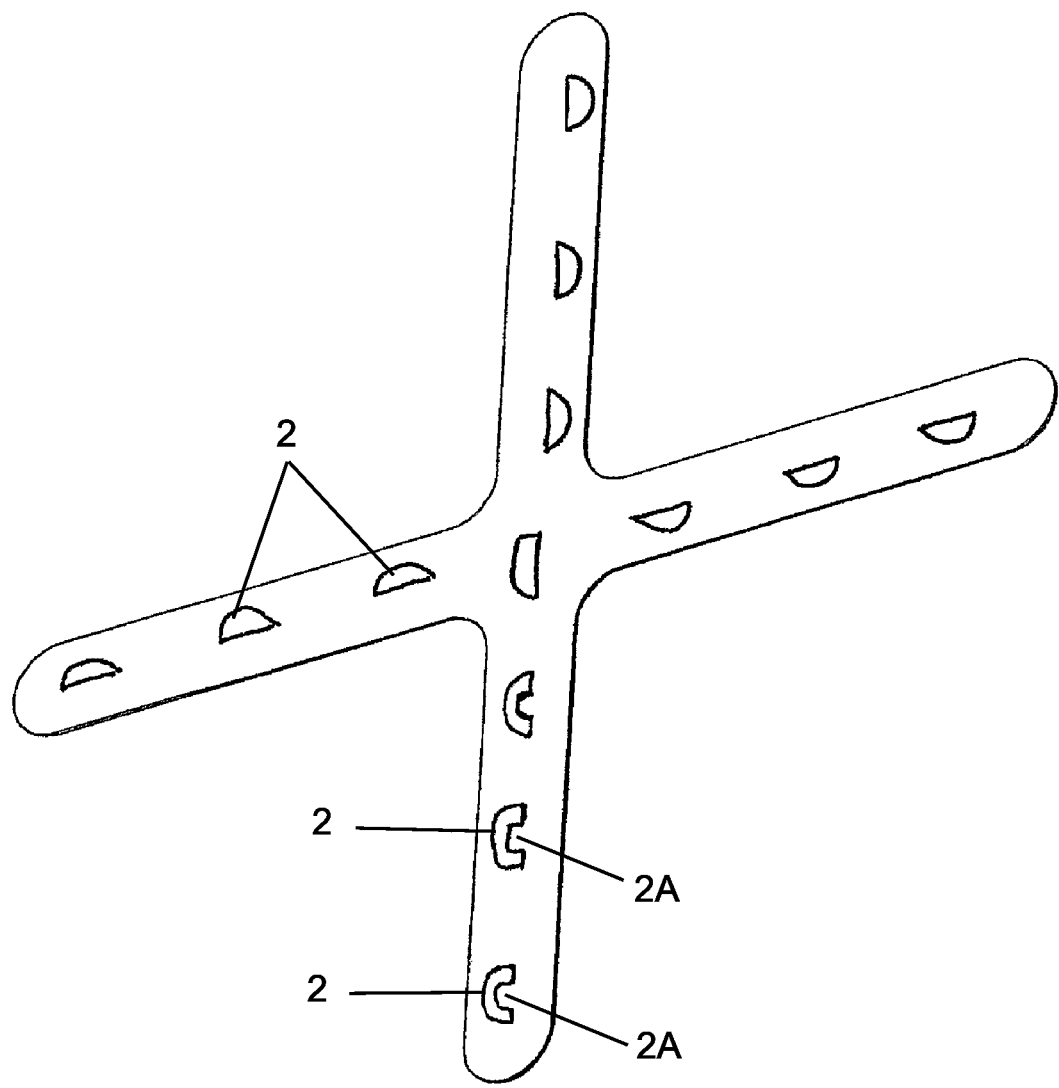
FIG. 2 is a perspective view of the metal shim of FIG. 1, in which holes have been formed.

The second stage of the manufacturing method is illustrated in FIG. 2. Holes 2 are punched, pressed or otherwise cut through the shim 1 in specifically determined positions. Any desired pattern can be used, depending upon the shape of the shim 1 and the intended final application for the surgical instrument; however, the holes 2 determine the locations of the cutting surfaces of the finished surgical instrument and therefore need to be located with accuracy. The holes 2 may be in the form of generally C-shaped or D-shaped slots, as illustrated, but other configurations are suitable as will be appreciated by a person skilled in the art. C-shaped slots mean that there is a tongue 2A which can be readily bent out of the plane of the shim to form a cutting surface, when desired.

Two alternative embodiments of the remaining steps of the manufacturing method will now be described.

Figure 3:
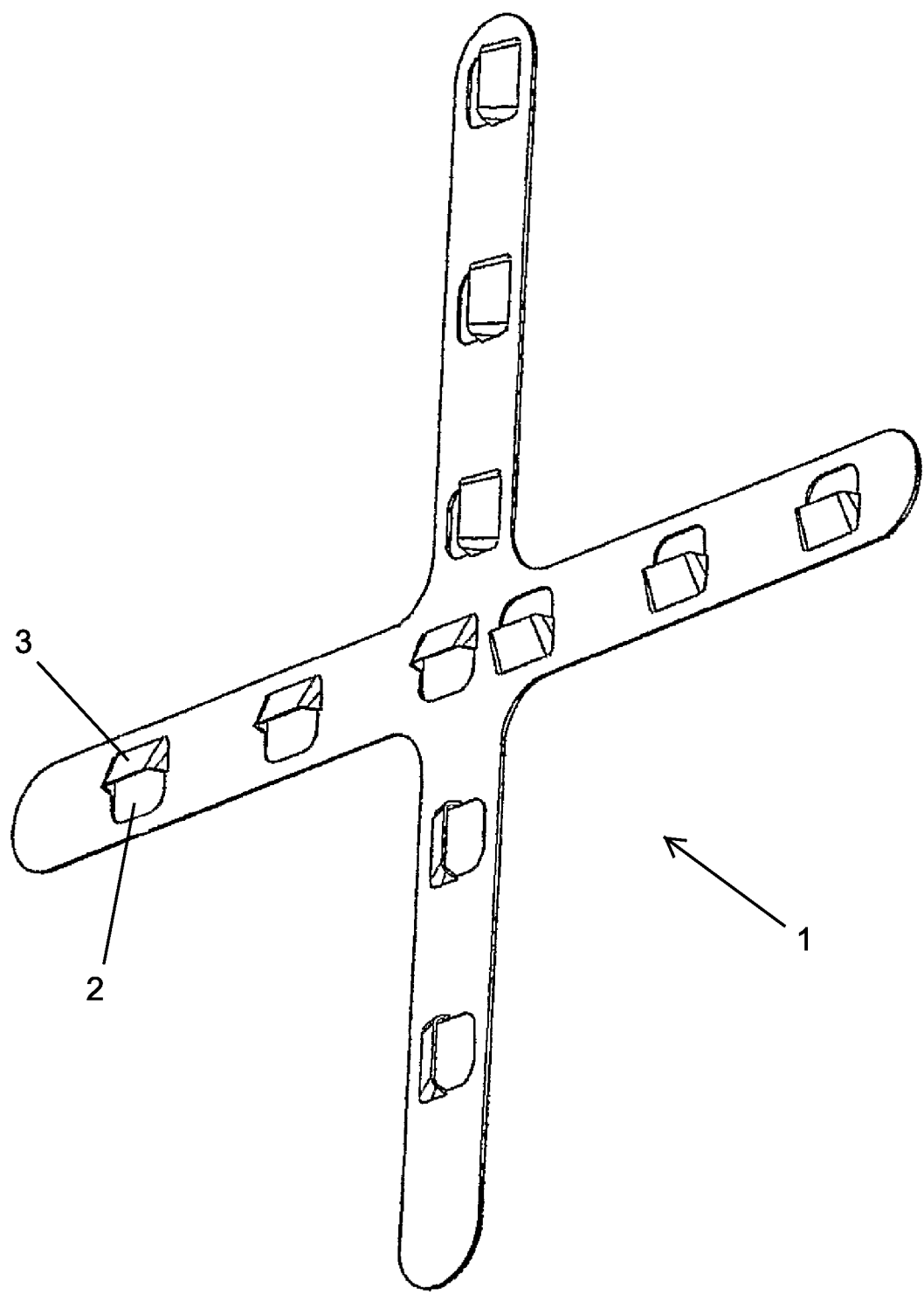
FIG. 3 is a perspective view of the metal shim of FIG. 1, in which cutting surfaces have been formed.

The first alternative embodiment is described with reference to FIGS. 3-10. Referring to FIG. 3, the next stage of the method is to form the cutting surfaces. At the location of each hole 2, metal remaining after the hole has been formed is bent out of the plane of the shim 1 in order to form a cutting surface 3. The shape and orientation of each cutting surface 3 is selected according to the shape of the shim 1 and the intended final application for the surgical instrument. Since the metal shim 1 is relatively thin (compared with the 1-1.5 mm thickness of a prior-art acetabular reamer cup), the cutting surfaces 3 may well be sharp enough for their intended purpose already, once formed, and therefore will not require additional sharpening by hand. However, if desired, a sharpening stage may be included in the manufacturing method, wherein the cutting surfaces 3 are sharpened by an automated process.

Figure 4:
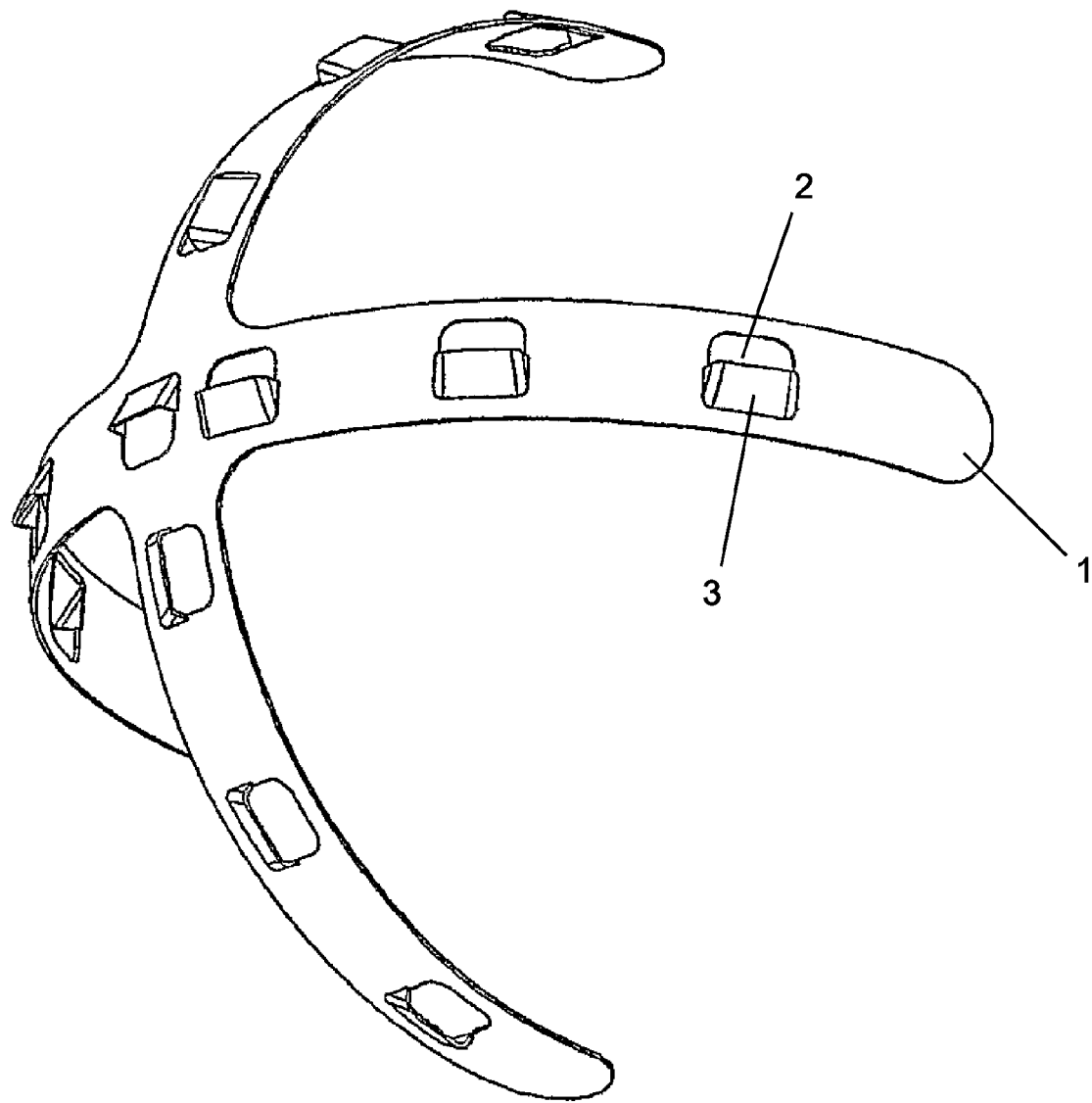
FIG. 4 is a perspective view of the metal shim of FIG. 3, having been pressed into a generally hemispherical shape.
Figure 5:
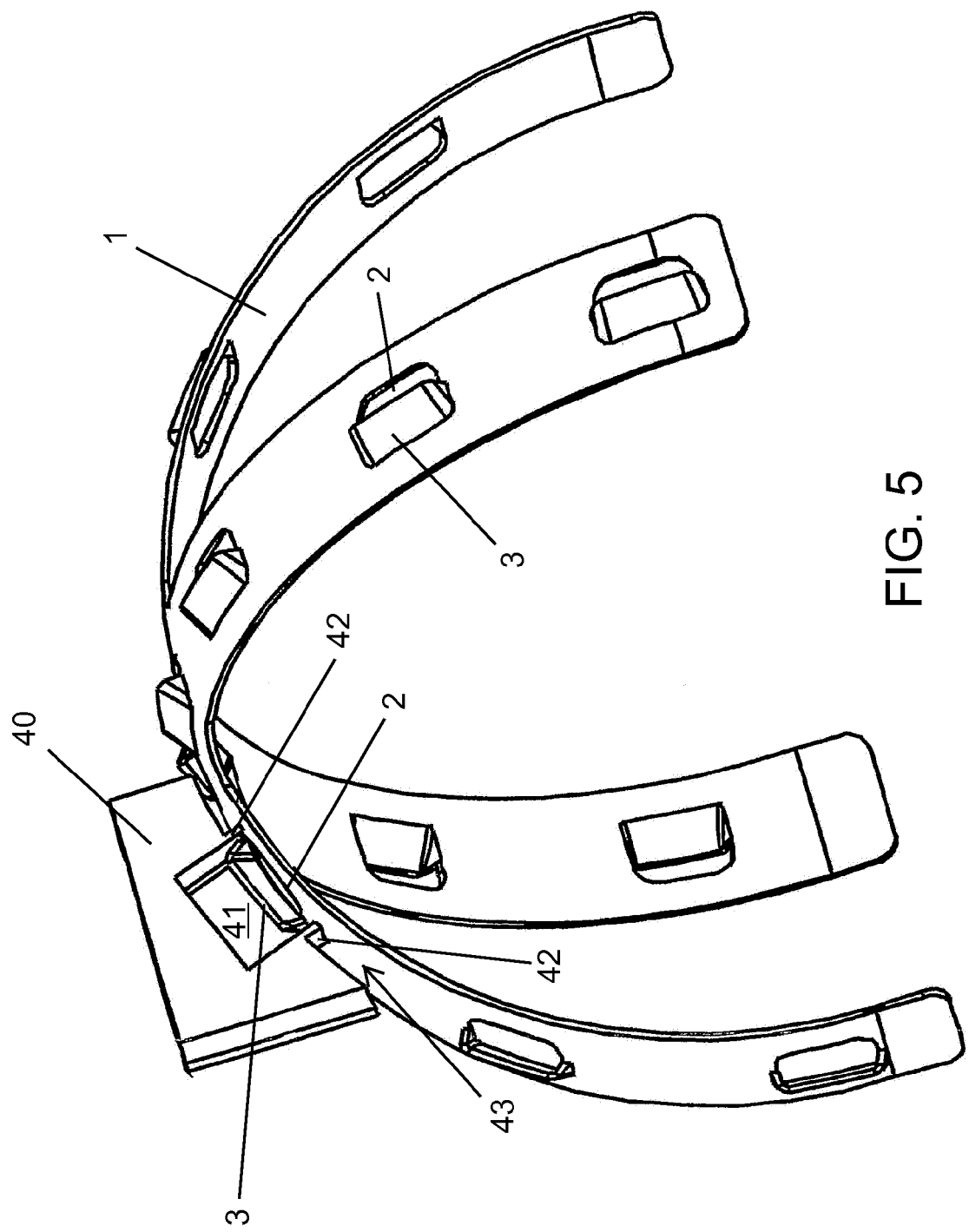
FIG. 5 is a perspective view of the metal shim of FIG. 4 illustrating how a mould tool shields one cutting surface during the moulding process.
Figure 6:
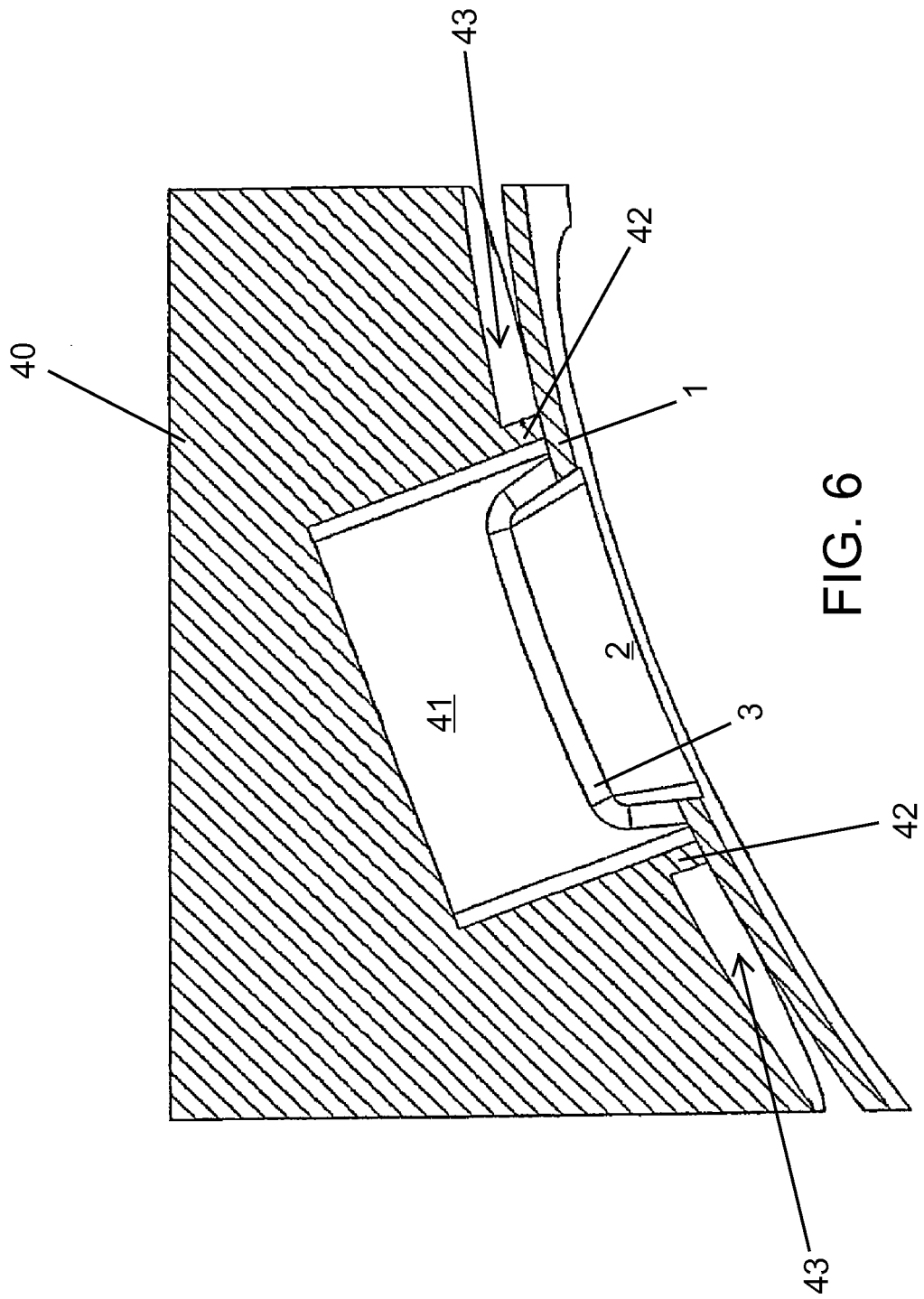
FIG. 6 is a cross-sectional side view of the mould tool and cutting surface of FIG. 5.
Figure 7:
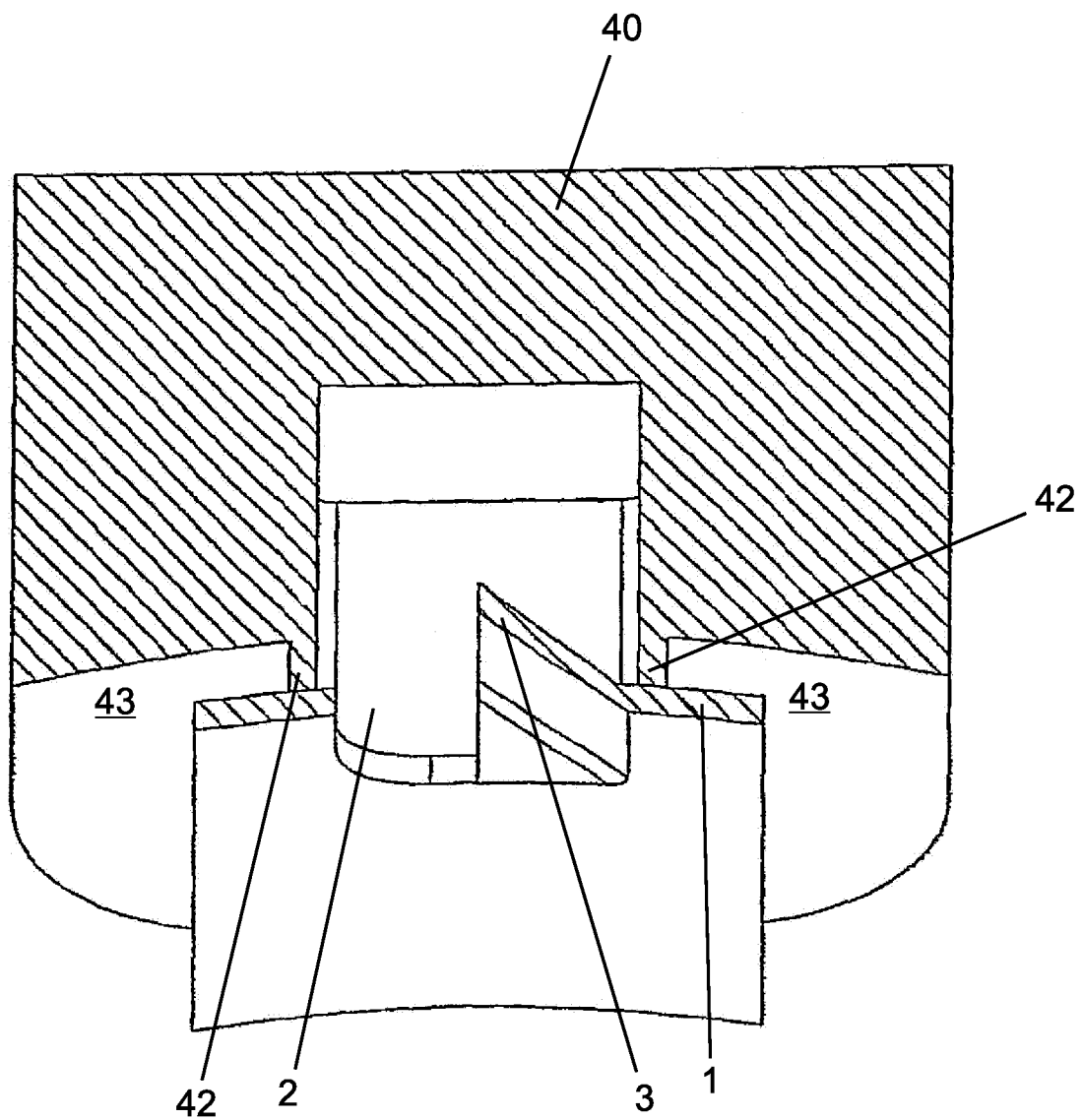
FIG. 7 is a cross-sectional view through the mould tool and cutting surface of FIG. 5.
Figure 8:
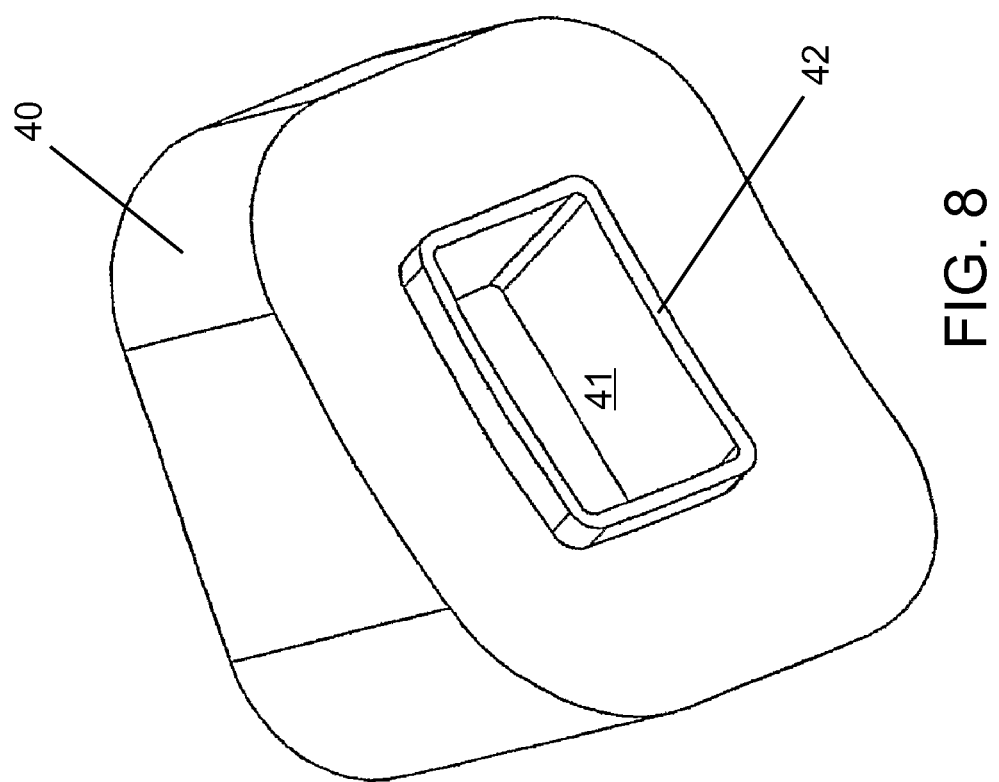
FIG. 8 is a perspective view, from below of part of the mould tool used to shield a cutting surface during the moulding process (the cutting surface is not illustrated)

Once the cutting surfaces 3 have been formed (and sharpened if necessary), the shim 1 is put into a press in order to bend it into a generally hemispherical shape, as illustrated in FIG. 4.

Having bent the shim 1 to the desired shape, the shim is placed in an injection moulder. A specially-designed mould tool is needed in order to temporarily shield the holes 2 and cutting surfaces 3 from the injection moulding process to prevent them filling with plastics, as both the holes and cutting surfaces obviously need to be exposed and free of plastics in the finished acetabular reamer.

Referring to FIGS. 5-8, part of a mould tool 40 is illustrated to show how the exterior of a cutting surface 3 is shielded from the moulding process. The mould tool 40 has a cavity 41 therein, in which the cutting surface 3 is located. The cavity 41 is defined by walls 42 which abut closely with the exterior surface of the shim 1. An undercut 43 defines the area into which plastics will flow during the moulding process, the close abutment between walls 42 and the exterior surface of the shim 1 preventing plastics from flowing into cavity 41.

For illustrative purposes, the shielding of only one cutting surface is shown in FIGS. 5-8, however in practice every cutting surface is similarly shielded and the whole moulding tool 40 has a generally hemispherical outer shape.

The interior of each cutting surface 3 also needs to be shielded from the moulding process. In one embodiment, this is achieved by using a spherical or hemispherical mould tool (not illustrated) which is closely located against the interior of shim 1 so as to prevent plastics from contacting any part of the interior of the shim during the moulding process. In an alternative embodiment, a mould tool (not illustrated) is used which is complementary in shape to that illustrated in FIG. 5 i.e. generally hemispherical and having cavities (equivalent to cavities 41) and walls (equivalent to walls 42) on the outer surface thereof which surround the holes 2 so as to prevent ingress of plastics. In this alternative embodiment, a reamer cup is formed in which the shim 1 is entirely encapsulated by the plastics substrate.

After the injection moulding process is completed, the mould tool 40 is removed, leaving a composite surgical instrument having an internal metal support [the shim 1], exposed metal cutting surfaces 3 and a plastics substrate 4.

Figure 9:
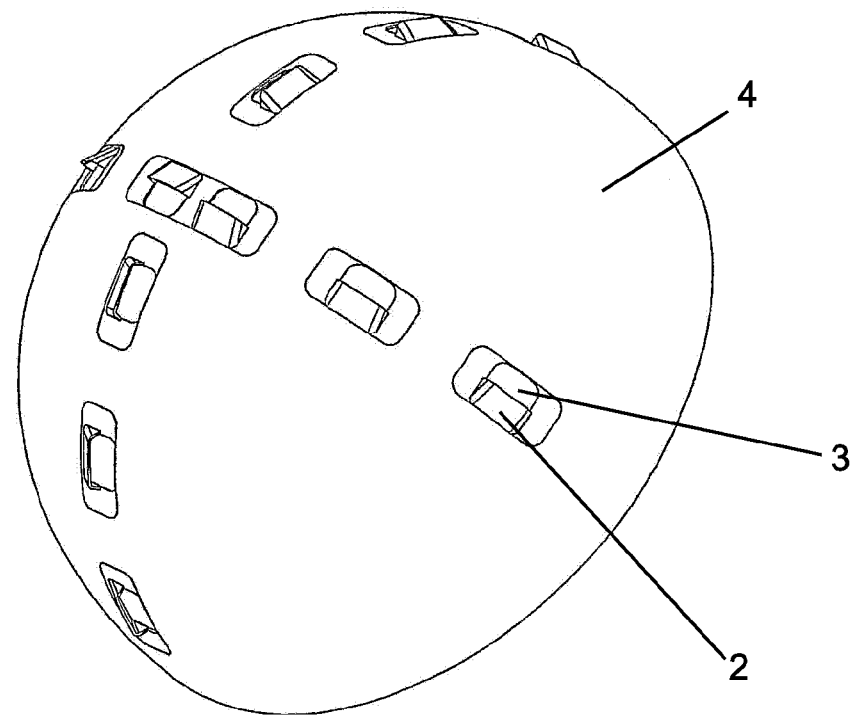
FIG. 9 is a perspective view of a the metal shim of FIG. 4 to which a plastics substrate has been overmoulded, resulting in a composite reamer cup.
Figure 10:
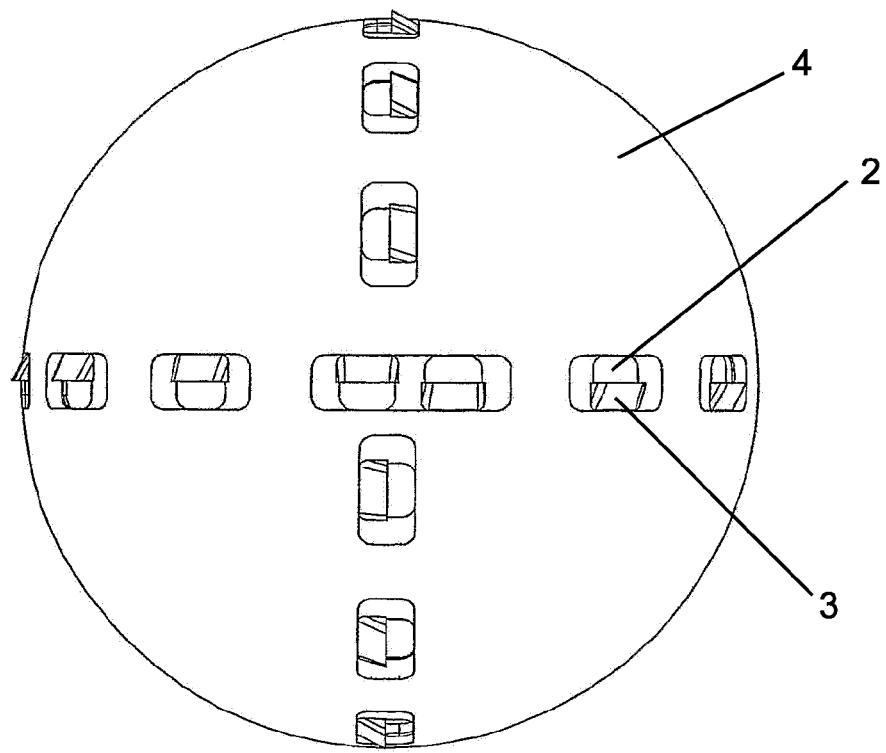
FIG. 10 is a top view of the reamer cup of FIG. 9.

As shown in FIGS. 9 and 10, after injection moulding, the shim 1 is covered (first embodiment) or encapsulated (alternative embodiment) by a plastics substrate 4 approximately 2.5 mm thick. In all embodiments, the cutting surfaces 3 are exposed. In this way, there is provided an acetabular reamer cup which is much more lightweight than the prior art reamer cups which are entirely made from metal. Metal shim 1 is thinner than the metal prior art reamer cups as it only needs to be of sufficient thickness to support the plastics substrate.

Figure 11:
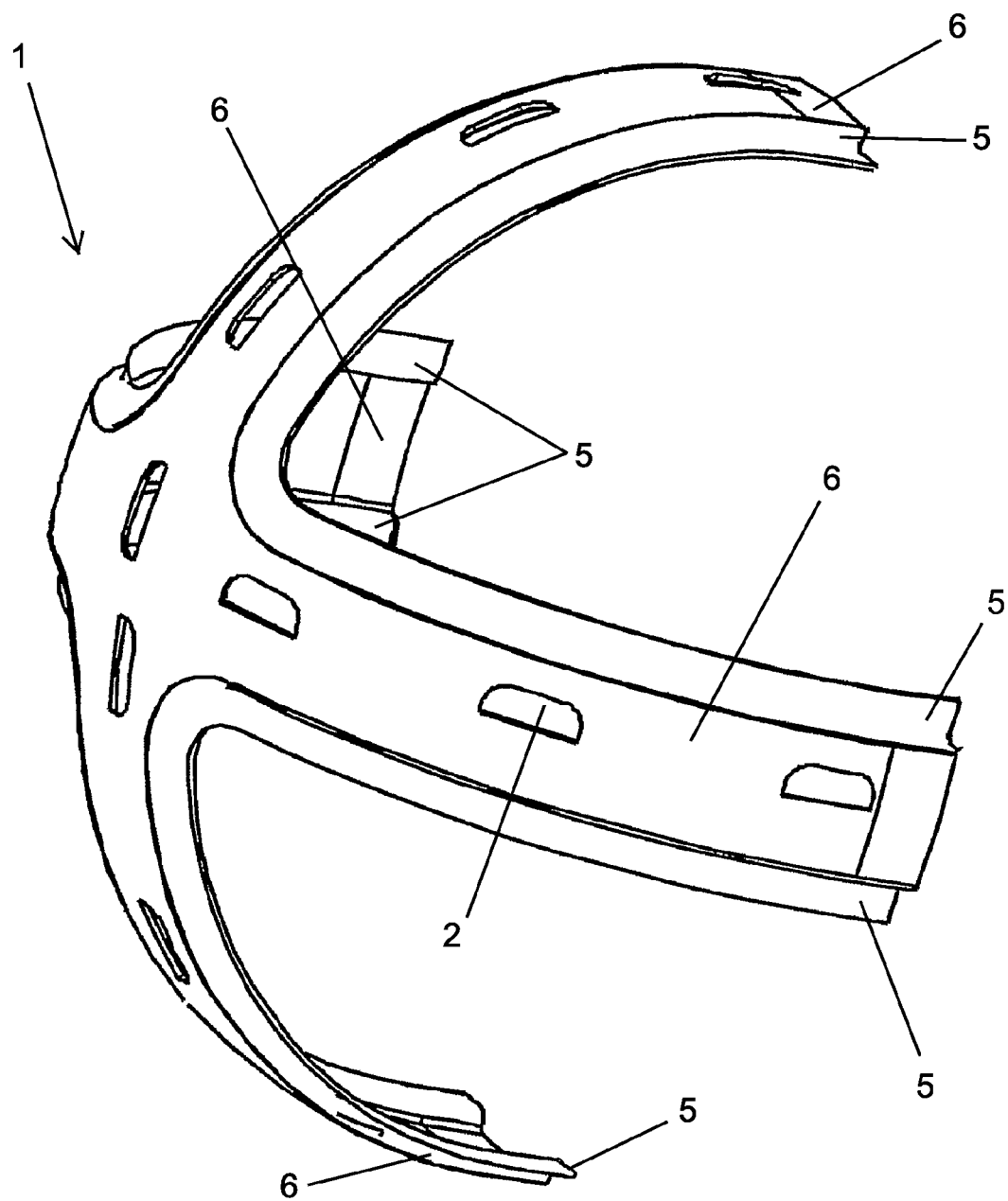
FIG. 11 is a perspective view of the metal shim of FIG. 2, having been pressed into a generally hemispherical shape.
Figure 12:
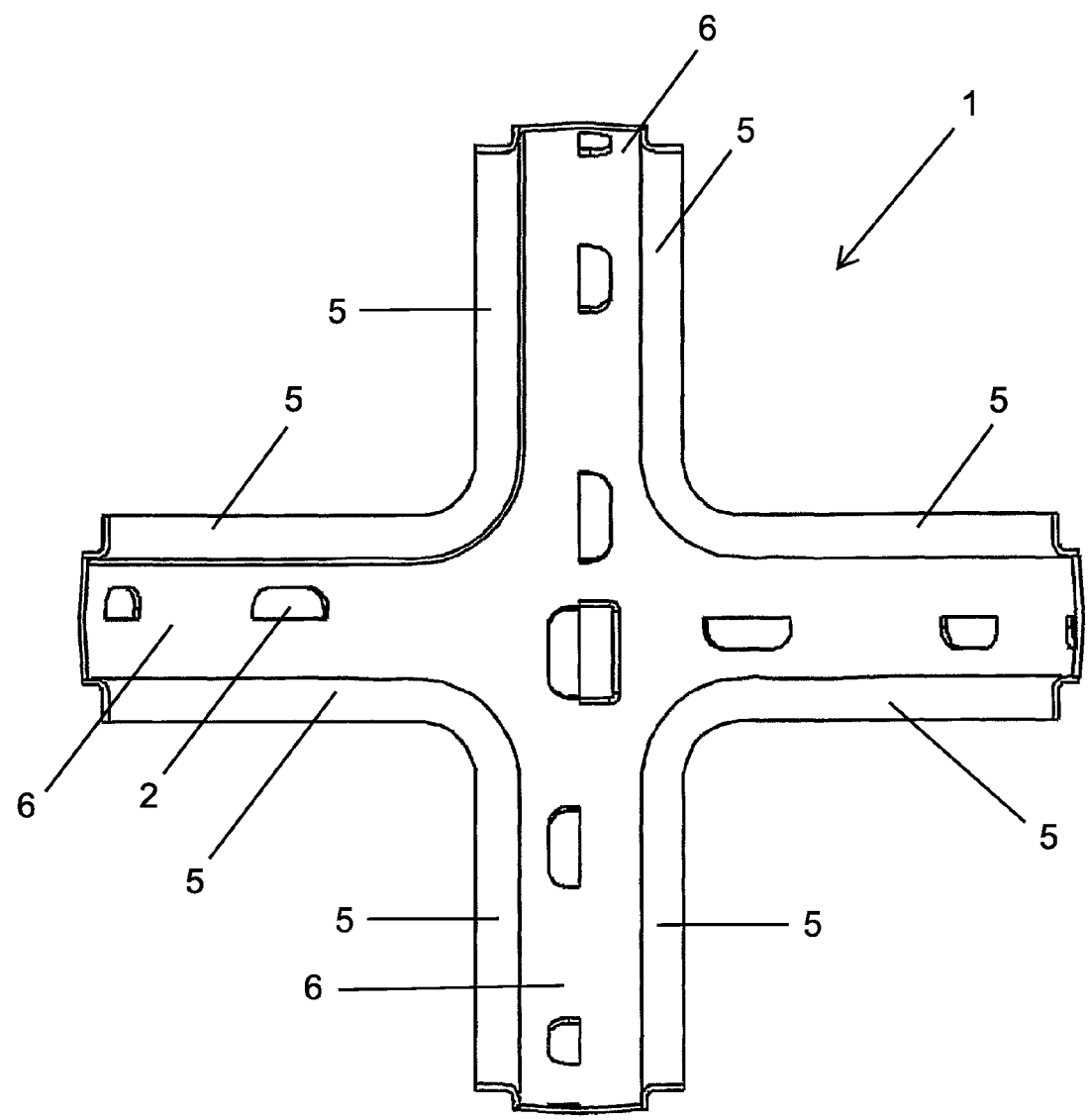
FIG. 12 is a top view of the shim of FIG. 11.

The second embodiment is described with reference to FIGS. 11-14. Taking the shim illustrated in FIG. 2, the shim is bent in a moulding tool or press (not illustrated) in order to bend it into a generally hemispherical shape as illustrated in FIG. 11. Simultaneously, or in a separate bending operation, a profile is bent transversely onto each limb of the shim, so that each limb has peripheral flanges 5 and a raised section 6 therebetween.

Having bent the shim 1 to the desired shape, the shim is placed in an injection moulder. A specially-designed mould tool is needed in order to temporarily shield the holes 2 from the injection moulding process to prevent them filling with plastics, as the holes need to be exposed and free of plastics after overmoulding, so that exposed cutting surfaces can be formed in the finished acetabular reamer.

Figure 13:
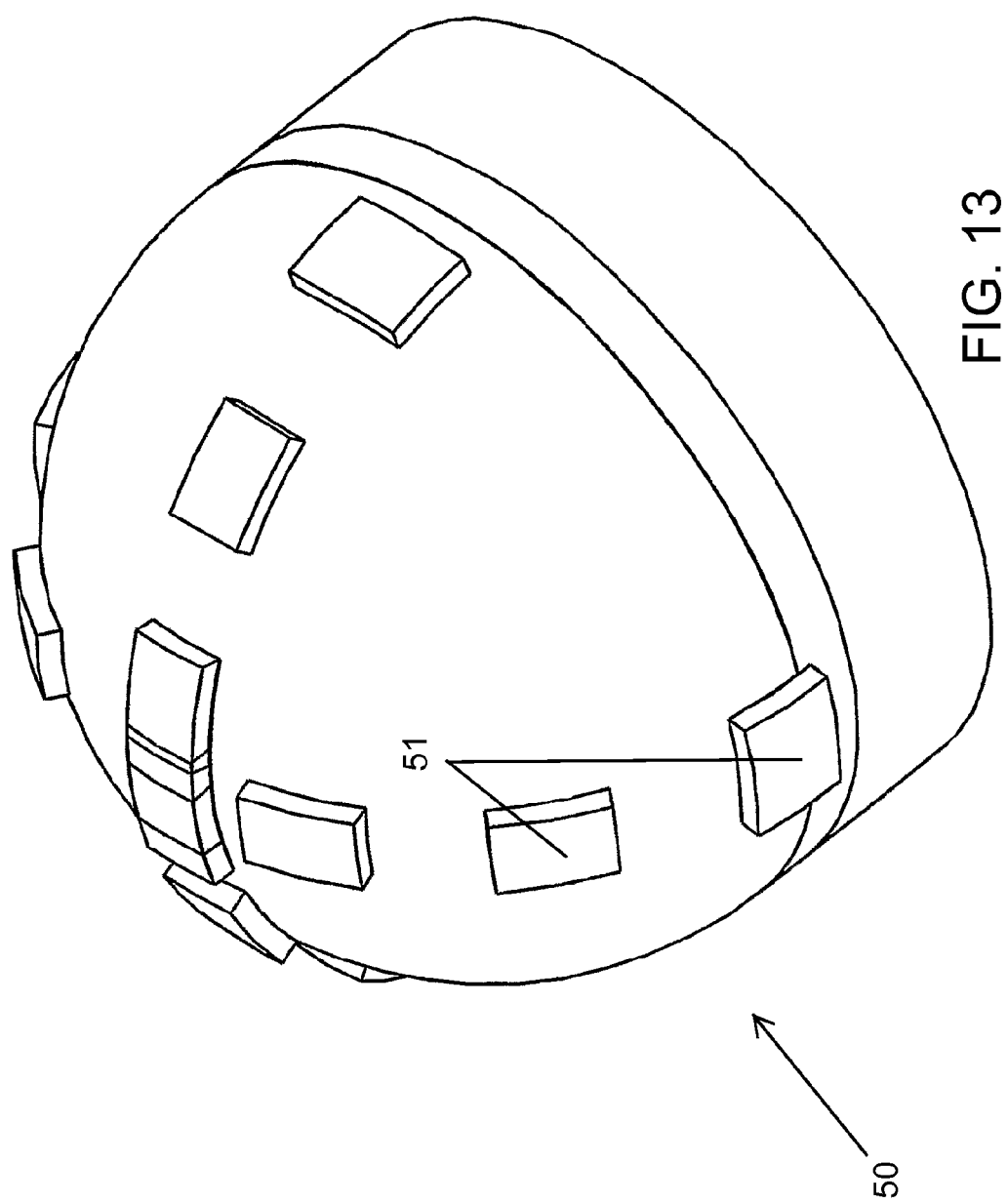
FIG. 13 is a perspective view of part of a mould tool.

Part of a suitable mould tool is illustrated in FIG. 13. The mould tool 50 has the same generally hemispherical shape as the bent shim 1. The mould tool is provided with a plurality of raised pads 51 over its surface. Importantly, these pads 51 are located such that they will align with the holes 2 of the bent shim 1, when the bent shim is placed on top of the mould tool 50. Preferably, the raised pads 51 fit closely inside the raised section 6 of the bent shim. In this way, the pads 51 effectively shield the underside of the raised section 6 in the vicinity of each hole 2 so that plastic does not encroach there during injection moulding. The underside of the raised section between the holes 2 (i.e. between the pads 51) is not shielded and therefore plastic can encroach there during injection moulding.

The top surface of the raised section 6 is shielded from the injection moulding plastics by means of a mating mould tool which is correspondingly hemispherical and which mates with the illustrated mould tool 50. When in position, the mating mould tool is in contact with the whole of the top surface of the raised section 6 so that it is shielded from the moulding process. The peripheral flanges 5 are not shielded by the mating mould tool and therefore plastic can encroach there during injection moulding.

Figure 14:
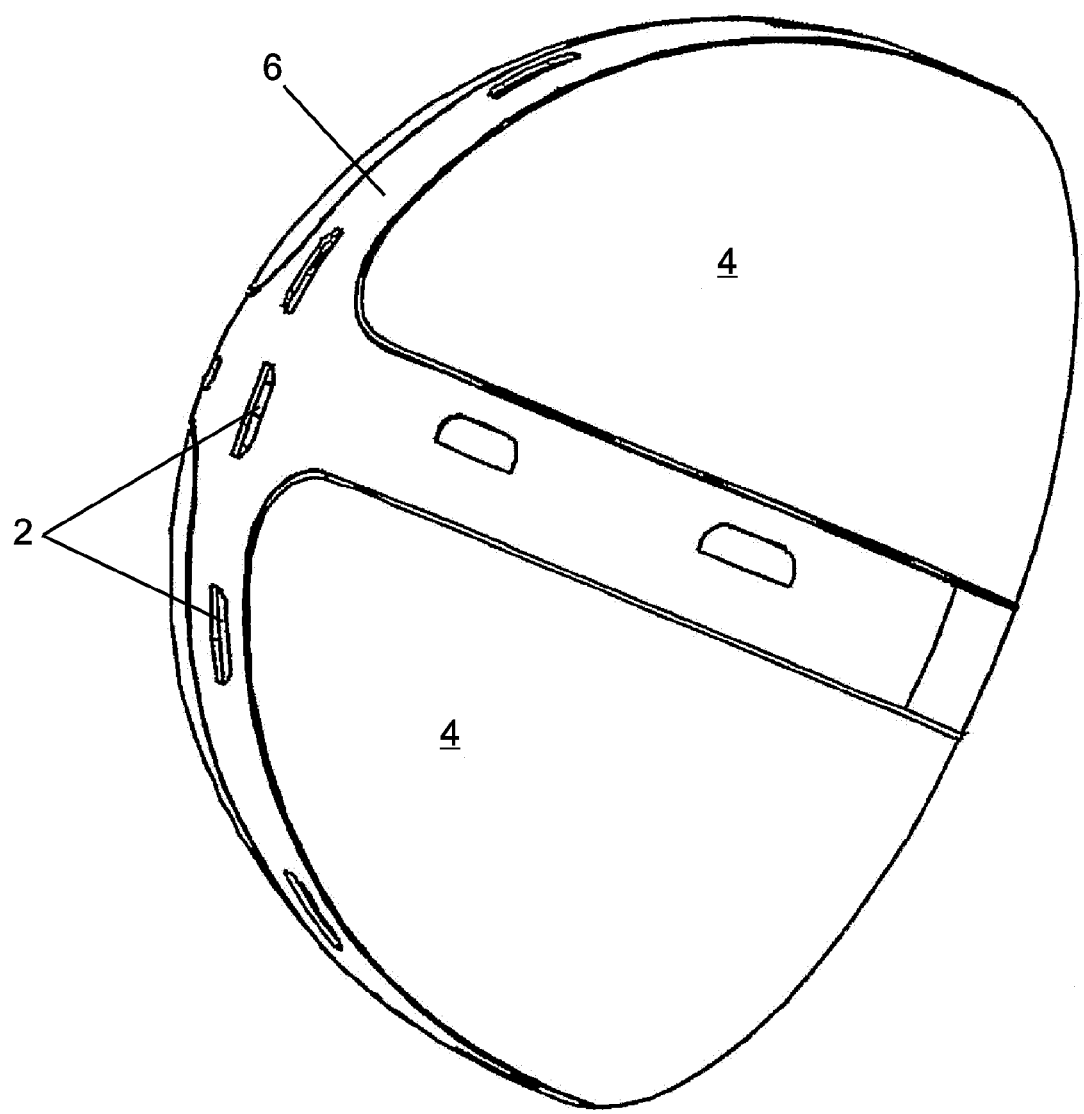
FIG. 14 is a perspective view of a the metal shim of FIGS. 11 and 12 to which a plastics substrate has been overmoulded and on which cutting surfaces have been formed, resulting in a composite reamer cup.

FIG. 14 shows how, after injection moulding, the shim 1 is covered by a plastics substrate 4 approximately 2.5 mm thick. The raised section 6 of the shim is exposed and preferably flush with the top surface of the substrate.

Cutting surfaces 3 are formed at each of the holes 2, for example using a broach.

In either embodiment, the plastic used in the injection moulding stage is preferably free-flowing acetal, although any medical-grade approved plastic may potentially be used.

Figure 15:
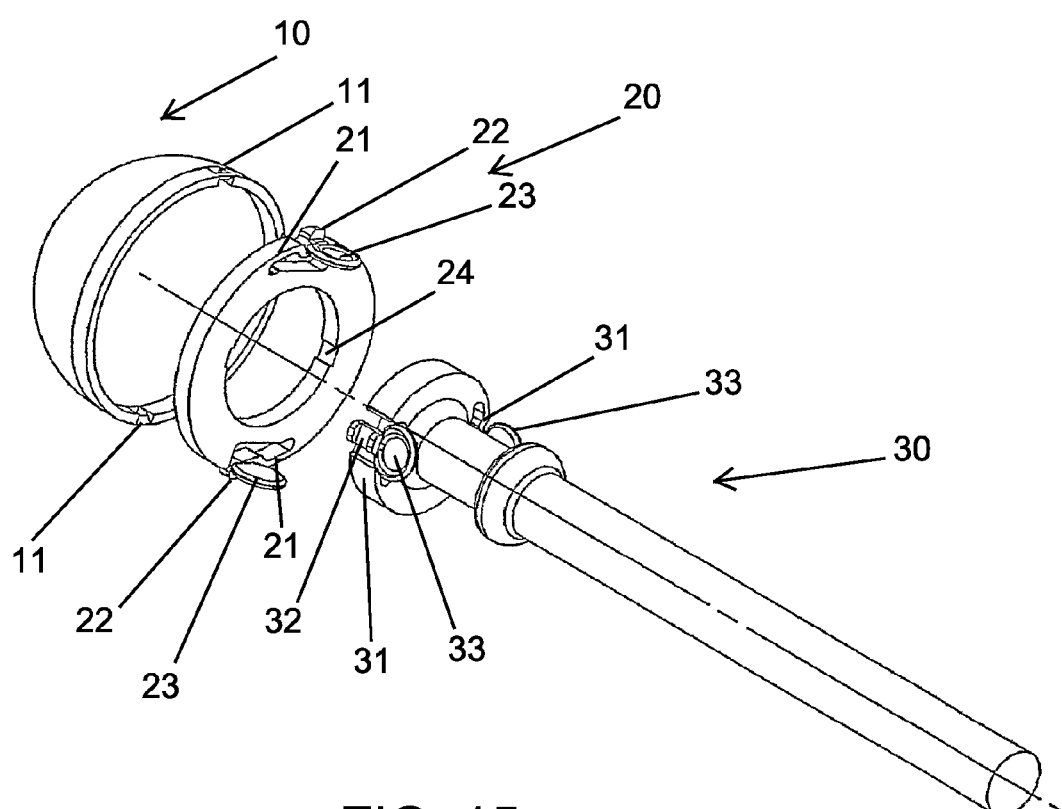
FIG. 15 is an exploded view of the reamer cup, connector and drive shaft, showing how they fit together, in use.

FIG. 15 shows how the finished reamer cup 10 is attached to a drive shaft 30. The cutting surfaces 3 are not illustrated in the schematic FIG. 15. The reamer cup 10 is attached to the drive shaft 30 by means of a generally annular connector 20.

The rim of the hemispherical reamer cup is provided with two diametrically located notches 11. The annular connector 20 is provided with two diametrically located resiliently flexible arms 21 which can be radially flexed inwardly by applying radially-inward finger pressure to pads 23, which are attached to the arms 21. Each of the flexible arms 21 is provided with a radially-protruding tag 22 at the extremity thereof.

In order to fit the connector 20 to the reamer cup 10, pads 23 are squeezed together so that flexible arms 21 (and hence tags 22) are moved radially-inwardly. The connector 20 is placed inside the rim of the reamer cup 10 with the tags 22 aligned with the notches 11. The pads 23 are then released so that the resiliently flexible arms 21 move radially-outwardly so that tags 22 locate in notches 11, thus holding the reamer cup 10 and connector 20 together.

One end of the drive shaft 30 is provided with two diametrically located resiliently flexible arms 31 which can be radially flexed inwardly by applying radially-inward finger pressure to pads 33, which are attached to the arms 31. Each of the flexible arms 31 is provided with a radially-protruding tag 32 at the extremity thereof.

In order to fit the drive shaft 30 to the connector 20, pads 33 are squeezed together so that flexible arms 31 (and hence tags 32) are moved radially-inwardly. The end of the drive shaft 30 is placed inside the annular connector 20 with the tags 32 aligned with notches 24 which are diametrically located on the interior surface of the connector 20. The pads 33 are then released so that the resiliently flexible arms 31 move radially-outwardly so that tags 32 locate in notches 24, thus holding the connector 20 and drive shaft 30 together. The tags 32 are preferably V-shaped (as illustrated) or similar so as to prevent relative axial movement of the connector 20 and drive shaft 30.

In this way, the reamer cup, connector and drive shaft are releasably attached to one another in such a way that a rotational driving force can be transmitted from the drive shaft 30 to the reamer cup 10. There is no need for pins, clips or other moving parts in order to fix the components together, the only moving parts being the flexible arms 21 and 31. The significant decrease in the number of components and moving parts greatly facilitates the cleaning of the connector and drive shaft (both of which can be reusable).

In use, the reamed bone particles might need to be retained and the particles can be readily retained within the hemispherical reamer cup.

The above-described method provides a greatly simplified and more cost-effective method of manufacturing surgical instruments, in particular a disposable acetabular reamer cup. The surgical instrument thus produced contains much less metal than conventionally-manufactured instruments and does not require hand-working. The cost-effective nature of the manufacturing method means that the instruments can be disposable. The method may equally be suitable for the manufacture of other orthopaedic surgical instruments, for example broaches/rasps, femoral reamers etc.

What is claimed is:

1. An orthopaedic surgical instrument, said instrument comprising:
   a non-planar shim having a plurality of holes or slots and at least one edge at respective ones of the holes or slots;
   a plastic substrate molded about said shim to substantially cover an exterior surface of said shim with the edges at the holes or slots being exposed; and
   wherein the exposed edges at the holes or slots in said shim include cutting surfaces.

2. The surgical instrument of claim 1, wherein said non-planar shim has a generally hemispherical shape.

3. The surgical instrument of claim 1, wherein said shim includes a plurality of connected limbs.

4. The surgical instrument of claim 3, wherein said shim is generally cross-shaped.

5. The surgical instrument of claim 1, wherein the holes or slots comprise closed holes or slots that are bounded by the respective edges of said shim.

6. The surgical instrument of claim 1, wherein said cutting surfaces are formed at the exposed edges at the holes or slots at portion of said shim that is bent relative to an adjacent surface of said shim.

7. The surgical instrument of claim 1, wherein said shim includes a peripheral flange with a raised section there between.

8. The surgical instrument of claim 7, wherein said plastic substrate is molded to an exterior surface of said peripheral flange.

9. An orthopaedic surgical instrument, said instrument comprising:
   a shim having a plurality of connected limbs and a generally hemispherical shape, wherein said shim comprises a plurality of holes or slots established at said limbs and wherein said shim comprises edges at respective ones of the holes or slots;
   a plastic substrate molded about said shim to substantially cover an exterior surface of said shim with the edges at the holes or slots being at least partially exposed; and
   wherein the exposed portions of the edges at the holes or slots in said shim include cutting surfaces.

10. The surgical instrument of claim 9, wherein said shim is generally cross-shaped.

11. The surgical instrument of claim 9, wherein the holes or slots comprise closed holes or slots that are bounded by the respective edges of said shim.

12. The surgical instrument of claim 9, wherein said cutting surfaces are formed at the edges at the holes or slots at a portion of said shim that is bent relative to an adjacent surface of said shim.

13. The surgical instrument of claim 12, wherein said plastic substrate forms a generally hemispherical shape about said shim, and wherein said cutting surfaces extend above a hemispherical outer surface of said plastic substrate.

14. The surgical instrument of claim 9, wherein said shim includes a peripheral flange with a raised section there between.

15. The surgical instrument of claim 14, wherein said plastic substrate is molded to an exterior surface of said peripheral flange.

16. The surgical instrument of claim 9 further comprising a rim, and wherein said rim includes notches, and wherein said notches are configured for connecting said surgical instrument with a drive shaft.

17. An orthopaedic surgical instrument, said instrument comprising:
   a plastic substrate formed about a metal support, said plastic substrate having a generally hemispherical shape; and
   cutting surfaces formed in said metal support and exposed relative to said plastic substrate.

18. The surgical instrument of claim 17, wherein said metal support includes a plurality of holes or slots with said cutting surfaces formed at the holes or slots on a portion of said shim that is bent relative to an adjacent surface of said shim.

19. The surgical instrument of claim 18, wherein said cutting surfaces extend above a hemispherical surface of said plastic substrate.

20. The surgical instrument of claim 17, wherein said metal support includes a plurality of connected limbs and a plurality of holes or slots established at said limbs with said cutting surfaces being formed at the holes or slots.

* * * * *